(12) United States Patent
Murphy et al.

(10) Patent No.: US 9,556,280 B2
(45) Date of Patent: Jan. 31, 2017

(54) ANTI-TFPI ANTIBODY VARIANTS WITH DIFFERENTIAL BINDING ACROSS PH RANGE FOR IMPROVED PHARMACOKINETICS

(71) Applicant: BAYER HEALTHCARE LLC, Tarrytown, NY (US)

(72) Inventors: John Murphy, Cambridge, MA (US); Zhuozhi Wang, Millbrae, CA (US); Ruth Winter, Oakland, CA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 117 days.

(21) Appl. No.: 14/213,278

(22) Filed: Mar. 14, 2014

(65) Prior Publication Data

US 2014/0275493 A1 Sep. 18, 2014

Related U.S. Application Data

(60) Provisional application No. 61/798,261, filed on Mar. 15, 2013.

(51) Int. Cl.
*C07K 16/38* (2006.01)

(52) U.S. Cl.
CPC .......... *C07K 16/38* (2013.01); *C07K 2317/14* (2013.01); *C07K 2317/30* (2013.01); *C07K 2317/55* (2013.01); *C07K 2317/56* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS 8,481,030 B2 *  7/2013  Wang ............... C07K 16/38
                                           424/133.1
8,613,919 B1 * 12/2013  Ma ................. C07K 16/38
                                           424/130.1

FOREIGN PATENT DOCUMENTS

WO  WO 2011/109452 A1    9/2011
WO  WO 2011111007 A2 *   9/2011  ............ C07K 16/40
WO  WO 2012/135671 A2   10/2012
WO  WO 2013/148248 A1   10/2013

OTHER PUBLICATIONS

Stryer, L. Biochemistry, 4th edition, W.H. Freeman and Co., 1995, pp. 18-23.*
Janeway et al., Immunobiology, 3rd edition, Garland Publishing Inc. 1997, pp. 3:1-3:11.*
Portolano et al., J Immunol. Feb. 1, 1993;150(3):880-7.*
Rudikoff et al., Proc Natl Acad Sci U S A. Mar. 1982;79(6):1979-83.*
Fundamental Immunology, William E. Paul, M.D. ed., 3d ed. 1993, p. 242.*
International Search Report, Application No. PCT/US2014/029048, Aug. 11, 2014.
Ito, et al., "The His-probe method: effects of histidine residues introduced into the completmentarity-determining regions of antibodies on antigen-antibody interactions at different pH values," *Fed of Euro Bio Soc.* (*FEBS*), 309(1):85-88 (Aug. 1992).

* cited by examiner

*Primary Examiner* — Michael Szperka

(57) ABSTRACT

Antibodies are disclosed that bind to and inhibit the anticoagulant function of TFPI and have a lower affinity for TFPI at pH 6.0 than at pH 7.4. The lower affinity at pH 6 improves circulating half-life (T½) due to reduced target mediated clearance, a process by which an antibody/antigen complex is endocytosed and trafficked to the lysosome where both components are degraded. The lower affinity at pH 6.0 results in disruption of the complex prior to lysosome targeting and allows for re-circulation of the antibody. Specific modifications to antibody binding by histidine residue substitution are disclosed along with methods of use.

6 Claims, 4 Drawing Sheets

FIGURE 1A. Variable Heavy Chain

FIGURE 1B. Variable Light Chain

Figure 3:
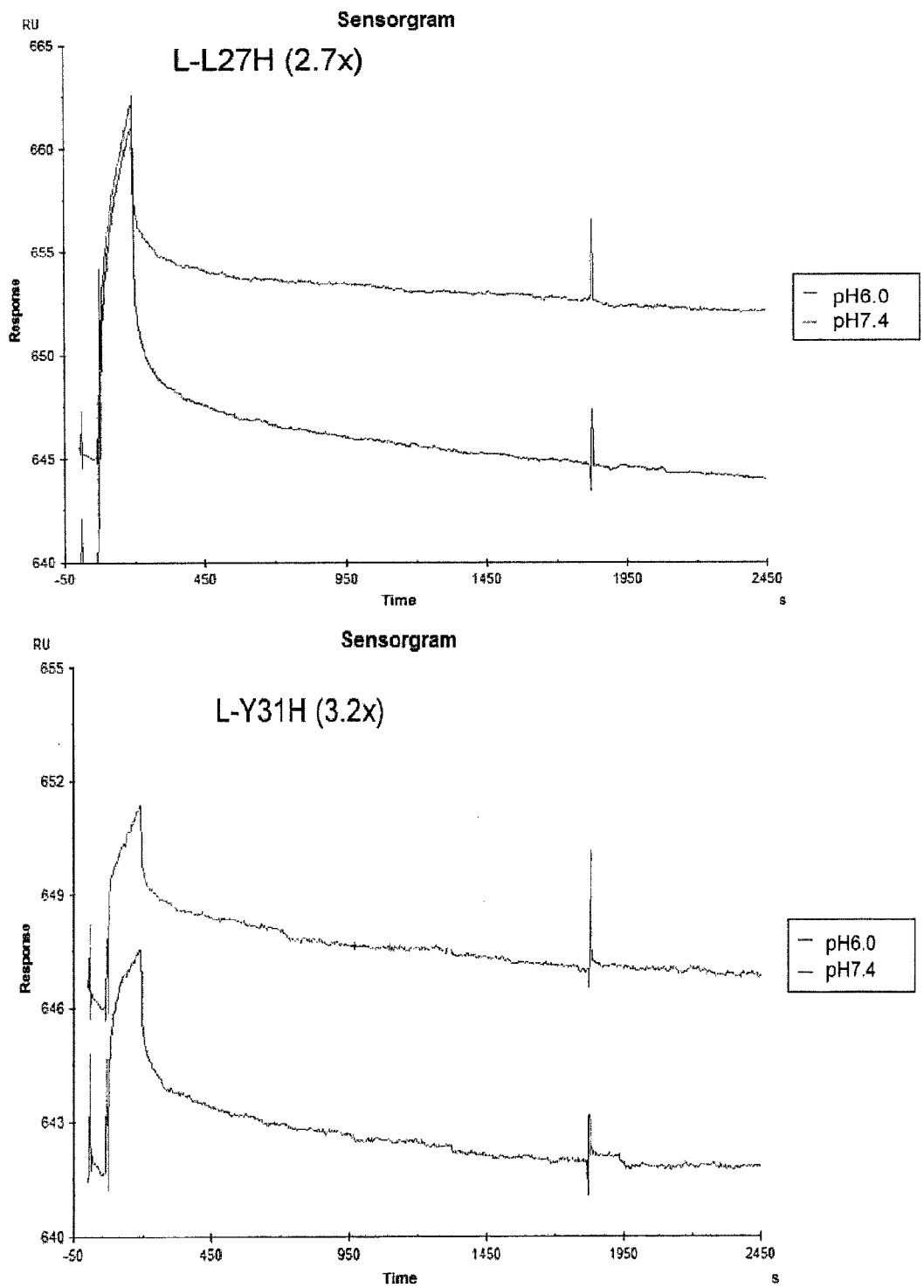

A. 40 possible His mutations on A200 heavy chain

```
                              --CDR1--          -------CDR2---------
EVQLVESGGGLVQPGGSLRLSCAASGFTFSSYGMDWVRQAPGKGLEWVSSIRGSRGSTYYADSVKGRFTISR
*                             **********           ********************

--CDR3--
DNSKNTLYLQMNSLRAEDTAVYYCARLYRYWFDYWGQGTLVTVSSAST
                              *********
```

Underlined: position of contact residues to TFPI
Asterisk: Proposed His mutations B. 29 possible mutations on A200 light chain

```
                              ---CDR1----          ----CDR2---
SYELTQPPSVSVSPGQTARITCSGDNLPKYYAHWYQQKPGQAPVVVIFYDVNRPSGIPERFSGSNSGNTAT
                              **********           ***********

---CDR3--
LTISGTQAMDEADYYCQAWWSSTPVFGGGTKLTVLGQPKAAPSVTLFPP
                              ********
```

Underlined: position of contact residues to TFPI
Asterisk"*": Proposed His mutation C. 40 possible His mutations on gB9.7 heavy chain

```
                              ---CDR1--          ----------CDR2--------
QVQLQQSGPGLVKPSQTLSLTCAISGDSVSSDSAAWSWIRQSPSRGLEWLGIIYYRSKWYNRYAVSVKSRITI
                              *********          *********************

---CDR3----
NPDTSKNQFSLQLNSVTPEDTAVYYCARWHSDKHWGFDDWGQGTLVT
                                 * *** *****
```

Underlined: position of contact residues to TFPI
Asterisk: Proposed His mutations D. 32 possible His mutations on gB9.7 light chain

```
                           ----CDR1--------                  --CDR2-
DIVMTQSPLSLPVTPGEPASISCRSSQSLVFRDGITYLNWYLQKPGQSPQLLIYKGSNRASGVPDRFSGSGSGTDF
                           ****************                  *******

--CDR3---
TLKISRVEAEDVGVYYCQQYDSYPLTFGQGTKVEIKRTVAAPSV
                    *********
```

Underlined: position of contact residues to TFPI
Asterisk: Proposed His mutations

Figure 2

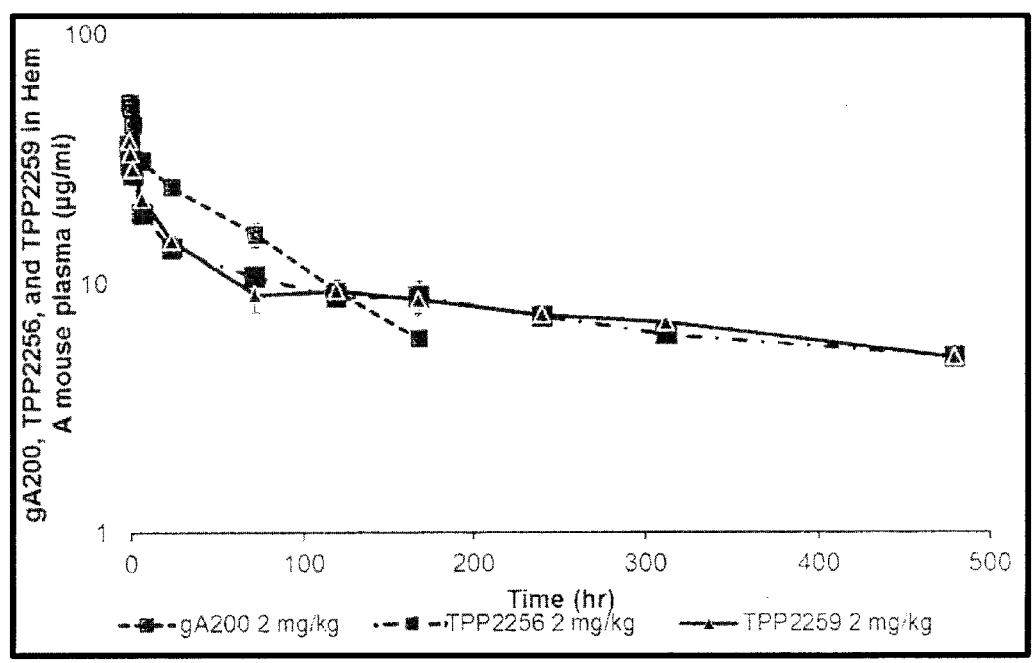
Figure 4. PK profiles of gA200, TPP2256 (L-Y31H/Y49H), and TPP2259 (L-Y31H) at 2 mg/kg

ANTI-TFPI ANTIBODY VARIANTS WITH DIFFERENTIAL BINDING ACROSS PH RANGE FOR IMPROVED PHARMACOKINETICS

CROSS-REFERENCE TO RELATED APPLICATIONS

This application claims the benefit of U.S. Provisional Application No. 61/798,261 filed Mar. 15, 2013, which application is incorporated herein by reference.

BACKGROUND

Currently the prophylactic management of hemophilia A and B patients is replacement of either FVIII or FIX (recombinant or plasma-derived products). These treatments are administered two or three times per week, placing a heavy burden on patients to comply with their prophylactic regime. Despite rigorous management and strict adherence, patients typically experience occasional breakthrough bleeds and require on-demand treatments. If not managed properly, frequent and severe bleeding leads to significant morbidities, especially hemarthropathy. Despite the proven efficacy of the existing agents used to treat hemophilia A and B patients, most adolescents, teenagers and older adults decide to lessen the burden of prophylaxis by reducing the number of injections taken on a routine basis. This approach further compromises the protection needed to adequately manage bleeds.

Consequently, an agent that significantly provides protection and requires relatively infrequent administration is most desired. The optimal therapy should provide protection via weekly or less frequent dosing. Given the current competitive environment, once a week therapies administered intravenously (i.v.) or subcutaneously (s.c.) may be a reality over the next 3-4 years. Therefore, an agent that is administered i.v. or s.c. should provide a superior administration profile with commensurate protection. In the event subcutaneous administration can be achieved, once a week dosing could also offer a significant value to the future treatment landscape due to the reduced invasiveness of this approach.

Another major issue for current hemophilia therapy is the development of inhibitory antibodies against Factor VIII or Factor IX. Approximately 25% of FVIII treated patients generate inhibitors, or neutralizing antibodies against FVIII. Inhibitors are also found in FIX treated patients, although less frequently. The development of inhibitors significantly reduces the effectiveness of replacement therapy and provides a challenge for managing bleeds in hemophilia patients. The current treatment for bleeds in patients with inhibitors to FVIII or FIX is bypass therapy with recombinant Factor VIIa or plasma derived FEIBA. The half-life of rFVIIa is quite short (~2 hours) and thus prophylactic treatment in these patients is uncommon [Blanchette, Haemophilia 16 (supplement 3): 46-51, 2010].

To address these unmet medical needs, antibodies against Tissue Factor Pathway Inhibitor (TFPI) as long-acting agents have been developed. See WO 2010/017196; WO 2011/109452; WO 2012/135671. TFPI is the major inhibitor of the tissue factor initiated coagulation pathway, which is intact in Persons with Hemophilia (PWH), and thus inhibition of TFPI may restore hemostasis in PWH exhibiting inhibitory antibodies to FVIII or FIX. In addition to allowing access to this target, monoclonal antibody (mAb) therapeutics have been shown to have significantly longer circulating half-lives (up to 3 weeks) than recombinant replacement factors. Antibodies that inhibit TFPI also have significant bioavailability following subcutaneous injection. Thus, anti-TFPI monoclonal antibody therapy would meet an important unmet medical need for subcutaneous, long acting hemostatic protection for PWH and PWH with inhibitors.

However, while inhibition of TFPI has been shown to promote coagulation in hemophilic plasmas and hemophilic animals, antibodies against TFPI have relatively short, non-linear half-lives due to a phenomenon known as target mediated drug disposition (TMDD) a process by which the antibody is removed from circulation due to its interaction with a rapidly cleared target or by being sequestered from the plasma due to its co-localization with its target, of the antibody:antigen complex. Therefore, antibodies that avoid TFPI mediated TMDD and have a prolonged half-life would lead to less frequent dosing and reduce the amount of material needed per dose. Furthermore, the need for a lower dose may also make feasible subcutaneous dosing where the dosing volume becomes a limiting step. For example, an optimized anti-TFPI antibody 2A8-g200 (WO 2011/109452), has a half-life of 28 hours when dosed at 5 mg/kg and 67 hrs when dosed at 20 mg/kg in non-human primates.

This relatively short half-life, and the need for larger doses to overcome TMDD, increases the injection burden on patients, limits formulation for subcutaneous dosing and increases the costs of goods. Pharmacokinetic analysis of these antibodies in non-human primates demonstrates that the circulating half-life is not linear with dose, and, particularly at lower doses, is shorter than is characteristic of antibody drugs. A similar pharmacokinetic profile was described in US2011/0318356 A1 for another anti-TFPI antibody. This differential, with a marked shortening of T½ at lower doses, is characteristic of TMDD, where the slower clearance at higher doses is due to saturation of the target.

Accordingly, an unmet medical need exists for better prophylactic treatment for moderate-to-severe hemophilia A and B, especially for those patients with inhibitors against FVIII or FIX. This need would be met by an anti-TFPI antibody having improved characteristics that may be administered intravenously or subcutaneously, and at a reduced frequency, preferably once weekly or less.

SUMMARY OF INVENTION

To increase the half-life of an anti-TFPI antibody and to reduce the injection burden, a longer acting anti-TFPI antibody was produced without a loss of efficacy and tested to confirm improved properties as compared to other anti-TFPI antibodies having demonstrated TFPI binding characteristics and proven efficacy in treating coagulation deficiencies. (See WO 2011/109452.) Specifically, TMDD is reduced by creating a variant anti-TFPI antibody having reduced affinity at pH 6.0 relative to pH 7.4. An anti-TFPI antibody may be taken into cells in complex with its target, TFPI, through receptors involved in TFPI clearance. One receptor, identified by Narita et al. (JBC 270 (42): 24800-4, 1995) is LRP (LDL receptor related protein), which targets TFPI for degradation in the endosome. However, if this antigen:antibody complex can be disrupted at low pH, which is characteristic of the endosome, the antibody can be recycled via FcRn binding, thereby increasing exposure in circulation. This principal has been shown for an antibody to PSCK9 by Chapparo-Riggers et al. JBC 287 (14): 110-7 (2012).

One method for disruption of an antigen:antibody complex at lower pH is to substitute histidine residues near the antibody:antigen interaction surface. The amino acid histidine (His) is protonated at low pH, near pH 6.0, and thus, a residue that is neutral at pH 7.4 acquires a positive charge at pH 6.0. This can lead to charge repulsion with other amino acids and a desirable degree of disruption or destabilization at the antibody:antigen interface.

To identify pH sensitive residues, the CDR amino acids and other amino acids involved in antigen:antibody binding of anti-TFPI antibodies (e.g. 2A8-g200) to TFPI antigen were changed individually to His. The individual His variants demonstrate differential binding at pH 7.4 vs. pH 6.0, and combinations of variants with differential binding have been tested for optimization.

Upon endosomal release, these pH sensitive anti-TFPI mAb variants bind to the neonatal FcRN receptor and are recycled to the plasma. Thus, a combination between a pH sensitive TFPI-binding site and a Fc domain with increased affinity for FcRN at low pH would have a synergistic effect that increases half-life, reduces the injection burden to patients, and reduces the cost of goods.

DESCRIPTION OF THE FIGURES

FIG. 1 shows alignment of amino acid sequences for 2A8-g200 and mutated anti-TFPI mAbs suitable for histidine substitution (SEQ ID NOs for these sequences can be found in Table 1). A. Variable Heavy Chain, B. Variable Light Chain. CDR regions 1-3 are indicated.

FIG. 2 shows synthesis and subcloning of a 2A8-g200 Fab Histidine Scanning Library. The CDR1-3 regions are indicated with a dashed line. Underlined amino acid residues indicate the position of contact residues to TFPI. An asterisk (*) indicates a proposed His mutation site. A). 2A8-g200 heavy chain; B) 2A8-g200 light chain; C). 4B7-gB9.7 heavy chain; and D) 4B7-gB9.7 light chain. Each of the SEQ. ID NOS shown in FIGS. 2A-2D can be associated with each known variant by referring to TABLE 1.

FIG. 3 shows dissociation constants at two pHs for the improved antibodies with exemplary histidine mutations: A. L-L27H and B. L-Y31H. Surface plasmon resonance (Biacore T200) was used to measure the dissociation rate of the antibodies.

FIG. 4 shows pK profiles observed in Hem A mouse plasma over time for several monoclonal antibodies at concentrations of 2 mg/kg: 2A8-g200 (- -■- -), histidine substituted monoclonal antibodies TPP2256 (L-Y31H/Y49H) (-·-▒-·-) and TPP2259 (L-Y31H) (-▲-). Pharmacokinetic parameters of the antibodies were determined after intravenous (i.v.) bolus administration to HemA mouse at 2 mg/kg.

DETAILED DESCRIPTION

The term "tissue factor pathway inhibitor" or "TFPI" as used herein refers to any variant, isoform and species homolog of human TFPI that is naturally expressed by cells. In a preferred embodiment of the invention, the binding of an antibody of the invention to TFPI reduces the blood clotting time.

As used herein, an "antibody" refers to a whole antibody and any antigen binding fragment (i.e., "antigen-binding portion") or single chain thereof. The term includes a full-length immunoglobulin molecule (e.g., an IgG antibody) that is naturally occurring or formed by normal immunoglobulin gene fragment recombinatorial processes, or an immunologically active portion of an immunoglobulin molecule, such as an antibody fragment, that retains the specific binding activity. Regardless of structure, an antibody fragment binds with the same antigen that is recognized by the full-length antibody. For example, an anti-TFPI monoclonal antibody fragment binds to an epitope of TFPI. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR); (vii) minibodies, diaboidies, triabodies, tetrabodies, and kappa bodies (see, e.g. Ill et al., Protein Eng 1997; 10:949-57); (viii) camel IgG; and (ix) IgNAR. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are analyzed for utility in the same manner as are intact antibodies.

Furthermore, it is contemplated that an antigen binding fragment may be encompassed in an antibody mimetic. The term "antibody mimetic" or "mimetic" as used herein is meant a protein that exhibits binding similar to an antibody but is a smaller alternative antibody or a non-antibody protein. Such antibody mimetic may be comprised in a scaffold. The term "scaffold" refers to a polypeptide platform for the engineering of new products with tailored functions and characteristics.

As used herein, the terms "inhibits binding" and "blocks binding" (e.g., referring to inhibition/blocking of binding of TFPI ligand to TFPI) are used interchangeably and encompass both partial and complete inhibition or blocking. Inhibition and blocking are also intended to include any measurable decrease in the binding affinity of TFPI to a physiological substrate when in contact with an anti-TFPI antibody as compared to TFPI not in contact with an anti-TFPI antibody, e.g., the blocking of the interaction of TFPI with factor Xa or blocking the interaction of a TFPI-factor Xa complex with tissue factor, factor VIIa or the complex of tissue factor/factor VIIa by at least about 10%, 20%, 30%, 40%, 50%, 60%, 70%, 80%, 90%, 95%, 96%, 97%, 98%, 99%, or 100%.

Therapeutic antibodies have been made through hybridoma technology described by Koehler and Milstein in "Continuous Cultures of Fused Cells Secreting Antibody of Predefined Specificity," Nature 256, 495-497 (1975). Fully human antibodies may also be made recombinantly in prokaryotes and eukaryotes. Recombinant production of an antibody in a host cell rather than hybridoma production is preferred for a therapeutic antibody. Recombinant production has the advantages of greater product consistency, likely higher production level, and a controlled manufacture that minimizes or eliminates the presence of animal-derived proteins. For these reasons, it is desirable to have a recombinantly produced monoclonal anti-TFPI antibody. The terms "monoclonal antibody" or "monoclonal antibody composition" as used herein refer to a preparation of antibody molecules of single molecular composition. A monoclonal antibody composition displays a single binding specificity and affinity for a particular epitope. Generally, therapeutic antibodies for human diseases have been generated using genetic engineering to create murine, chimeric, humanized or fully human antibodies. Murine monoclonal antibodies were shown to have limited use as therapeutic agents because of a short serum half-life, an inability to trigger human effector functions, and the production of human anti-mouse-antibodies (Brekke and Sandlie, "Therapeutic Antibodies for Human Diseases at the Dawn of the Twenty-first Century," Nature 2, 53, 52-62, January 2003). Chimeric antibodies have been shown to give rise to human anti-chimeric antibody responses. Humanized antibodies further minimize the mouse component of antibodies. However, a fully human antibody avoids the immunogenicity associated with murine elements completely. Thus, there is a need to develop antibodies that are human or humanized to a degree necessary to avoid the immunogenicity associated with other forms of genetically engineered monoclonal antibodies. In particular, chronic prophylactic treatment such as would be required for hemophilia treatment with an anti-TFPI monoclonal antibody has a high risk of development of an immune response to the therapy if an antibody with a murine component or murine origin is used due to the frequent dosing required and the long duration of therapy. For example, antibody therapy for hemophilia A may require weekly dosing for the lifetime of a patient. This would be a continual challenge to the immune system. Thus, the need exists for a fully human antibody for antibody therapy for hemophilia and related genetic and acquired deficiencies or defects in coagulation. Accordingly, the term "human monoclonal antibody" refers to antibodies displaying a single binding specificity which have at least portions of variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). These human antibodies include chimeric antibodies, such as mouse/human and humanized antibodies that retain non-human sequences.

An "isolated antibody," as used herein, is intended to refer to an antibody which is substantially free of other antibodies having different antigenic specificities (e.g., an isolated antibody that binds to TFPI is substantially free of antibodies that bind antigens other than TFPI). An isolated antibody that binds to an epitope, isoform or variant of human TFPI may, however, have cross-reactivity to other related antigens, e.g., from other species (e.g., TFPI species homologs). Moreover, an isolated antibody may be substantially free of other cellular material and/or chemicals.

As used herein, "specific binding" refers to antibody binding to a predetermined antigen. Typically, the antibody binds with an affinity of at least about $10^5$ and binds to the predetermined antigen with an affinity that is higher, for example at least two-fold greater, than its affinity for binding to an irrelevant antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, the term "high affinity" for an IgG antibody refers to a binding affinity of at least about $10^7$, in some embodiments at least about $10^8$, in some embodiments at least about $10^9$, $10^{10}$, $10^{11}$ or greater, e.g., up to $10^{13}$ or greater. However, "high affinity" binding can vary for other antibody isotypes. For example, "high affinity" binding for an IgM isotype refers to a binding affinity of at least about $1.0 \times 10^7$. As used herein, "isotype" refers to the antibody class (e.g., IgM or IgG1) that is encoded by heavy chain constant region genes.

"Complementarity-determining region" or "CDR" refers to one of three hypervariable regions within the variable region of the heavy chain or the variable region of the light chain of an antibody molecule that form the N-terminal antigen-binding surface that is complementary to the three-dimensional structure of the bound antigen. Proceeding from the N-terminus of a heavy or light chain, these complementarity-determining regions are denoted as "CDR1," "CDR2," and "CDR3," respectively. CDRs are involved in antigen-antibody binding, and the CDR3 comprises a unique region specific for antigen-antibody binding. An antigen-binding site, therefore, may include six CDRs, comprising the CDR regions from each of a heavy and a light chain V region.

As used herein, except with respect to the individual or plurality of histidine substitutions described below, "conservative substitutions" refers to modifications of a polypeptide that involve the substitution of one or more amino acids for amino acids having similar biochemical properties that do not result in loss of a biological or biochemical function of the polypeptide. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). It is envisioned that the antibodies of the present invention may have conservative amino acid substitutions and still retain activity.

The term "substantial homology" indicates that two polypeptides, or designated sequences thereof, when optimally aligned and compared, are identical, with appropriate amino acid insertions or deletions, in at least about 80% of amino acids, usually at least about 85%, preferably about 90%, 91%, 92%, 93%, 94%, or 95%, more preferably at least about 96%, 97%, 98%, 99%, 99.1%, 99.2%, 99.3%, 99.4%, or 99.5% of the amino acids. The invention includes polypeptide sequences having substantial homology to the specific amino acid sequences recited herein.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, such as the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40.

Another method for determining the best overall match between a query sequence (a sequence of the present invention) and a subject sequence, also referred to as a global sequence alignment, can be determined using the CLUSTALW computer program (Thompson et al., Nucleic Acids Research, 1994, 2(22): 4673-4680), which is based on the algorithm of Higgins et al., (Computer Applications in the Biosciences (CABIOS), 1992, 8(2): 189-191). In a sequence alignment the query and subject sequences are both DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty=10, Gap Extension Penalty=0.1. For multiple alignments, the following CLUSTALW parameters are preferred: Gap Opening Penalty=10, Gap Extension Parameter=0.05; Gap Separation Penalty Range=8; % Identity for Alignment Delay=40.

Also provided are pharmaceutical compositions comprising therapeutically effective amounts of anti-TFPI monoclonal antibody and a pharmaceutically acceptable carrier. As used herein, "therapeutically effective amount" means an amount of an anti-TFPI monoclonal antibody variant or of a combination of such antibody and factor VIII or factor IX that is needed to effectively increase the clotting time in vivo or otherwise cause a measurable benefit in vivo to a patient in need. The precise amount will depend upon numerous factors, including, but not limited to the components and physical characteristics of the therapeutic composition, intended patient population, individual patient considerations, and the like, and can readily be determined by one skilled in the art. "Pharmaceutically acceptable carrier" is a substance that may be added to the active ingredient to help formulate or stabilize the preparation and causes no significant adverse toxicological effects to the patient. Examples of such carriers are well known to those skilled in the art and include water, sugars such as maltose or sucrose, albumin, salts such as sodium chloride, etc. Other carriers are described for example in Remington's Pharmaceutical Sciences by E. W. Martin. Such compositions will contain a therapeutically effective amount of at least one anti-TFPI monoclonal antibody.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. The composition is preferably formulated for parenteral injection. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In some cases, it will include isotonic agents, for example, sugars, polyalcohols such as mannitol, sorbitol, or sodium chloride in the composition.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

The human monoclonal antibody can be used for therapeutic purposes for treating genetic and acquired deficiencies or defects in coagulation. For example, the human monoclonal antibodies may be used to block the interaction of TFPI with FXa, or to prevent TFPI-dependent inhibition of the TF/FVIIa activity. Additionally, the human monoclonal antibody may also be used to restore the TF/FVIIa-driven generation of FXa to bypass the insufficiency of FVIII- or FIX-dependent amplification of FXa.

The human monoclonal antibodies have therapeutic use in the treatment of disorders of hemostasis such as thrombocytopenia, platelet disorders and bleeding disorders (e.g., hemophilia A, hemophilia B and hemophilia C). Such disorders may be treated by administering a therapeutically effective amount of the anti-TFPI monoclonal antibody variant to a patient in need thereof. The human monoclonal antibodies also have therapeutic use in the treatment of uncontrolled bleeds in indications such as trauma and hemorrhagic stroke. Thus, also provided is a method for shortening the bleeding time comprising administering a therapeutically effective amount of an anti-TFPI human monoclonal antibody variant of the invention to a patient in need thereof.

The antibodies can be used as monotherapy or in combination with other therapies to address a hemostatic disorder. For example, co-administration of one or more variant antibodies of the invention with a clotting factor such as factor VIIa, factor VIII or factor IX is believed useful for treating hemophilia. In a separate embodiment, Factor VIII or Factor IX are administered in the substantial absence of Factor VII. "Factor VII" includes factor VII and factor VIIa.

A method for treating genetic and acquired deficiencies or defects in coagulation comprises administering (a) a first amount of a variant monoclonal antibody that binds to human tissue factor pathway inhibitor and (b) a second amount of factor VIII or factor IX, wherein said first and second amounts together are effective for treating said deficiencies or defects. Similarly, a method for treating genetic and acquired deficiencies or defects in coagulation comprises administering (a) a first amount of a monoclonal antibody variant that binds to human tissue factor pathway inhibitor and (b) a second amount of factor VIII or factor IX, wherein said first and second amounts together are effective for treating said deficiencies or defects, and further wherein factor VII is not coadministered. The invention also includes a pharmaceutical composition comprising a therapeutically effective amount of the combination of a monoclonal antibody variant of the invention and factor VIII or factor IX, wherein the composition does not contain factor VII.

These combination therapies are likely to reduce the necessary infusion frequency of the clotting factor. By co-administration or combination therapy is meant administration of the two therapeutic drugs each formulated separately or formulated together in one composition, and, when formulated separately, administered either at approximately the same time or at different times, but over the same therapeutic period.

In some embodiments, one or more antibody variants described herein can be used in combination to address a hemostatic disorder. For example, co-administration of two or more of the antibody variants described herein is believed useful for treating hemophilia or other hemostatic disorder.

The pharmaceutical compositions may be parenterally administered to subjects suffering from hemophilia A or B at a dosage and frequency that may vary with the severity of the bleeding episode or, in the case of prophylactic therapy, may vary with the severity of the patient's clotting deficiency.

The compositions may be administered to patients in need as a bolus or by continuous infusion. For example, a bolus administration of an antibody variant present as a Fab fragment may be in an amount of from 0.0025 to 100 mg/kg body weight, 0.025 to 0.25 mg/kg, 0.010 to 0.10 mg/kg or 0.10-0.50 mg/kg. For continuous infusion, an antibody variant present as an Fab fragment may be administered at 0.001 to 100 mg/kg body weight/minute, 0.0125 to 1.25 mg/kg/min., 0.010 to 0.75 mg/kg/min., 0.010 to 1.0 mg/kg/min. or 0.10-0.50 mg/kg/min. for a period of 1-24 hours, 1-12 hours, 2-12 hours, 6-12 hours, 2-8 hours, or 1-2 hours. For administration of an antibody variant present as a full-length antibody (with full constant regions), dosage amounts may be about 1-10 mg/kg body weight, 2-8 mg/kg, or 5-6 mg/kg. Such full-length antibodies would typically be administered by infusion extending for a period of thirty minutes to three hours. The frequency of the administration would depend upon the severity of the condition. Frequency could range from three times per week to once every two weeks to six months.

Additionally, the compositions may be administered to patients via subcutaneous injection. For example, a dose of 10 to 100 mg anti-TFPI antibody can be administered to patients via subcutaneous injection weekly, biweekly or monthly.

Variant monoclonal antibodies to human tissue factor pathway inhibitor (TFPI) are provided. Further provided are the isolated nucleic acid molecules encoding the same. Pharmaceutical compositions comprising the variant anti-TFPI monoclonal antibodies and methods of treatment of genetic and acquired deficiencies or defects in coagulation such as hemophilia A and B are also provided. Also provided are methods for shortening the bleeding time by administering an anti-TFPI monoclonal antibody to a patient in need thereof. Methods for producing a variant monoclonal antibody that binds human TFPI according to the present disclosure are also provided.

The therapeutic composition comprises antibody having binding regions that differ from the sequence of a parenteral TFPI binding antibody by the intentional selection or engineering of one or more substitutions of the amino acid histidine (H, HIS) for at least one native amino acid as defined in the parental sequence. The amino acid change confers longer circulating half-life T½ relative to the parental molecule.

An antibody specific for TFPI that binds to TFPI with at least 20% lower efficiency at pH 6.0 than at pH 7.0 is disclosed and that shows an improvement in circulating T½ of approximately 400%. The beneficial effect reducing TMDD is demonstrated for an antibody or antibody binding region that differs from the sequence of a target antibody such as 2A8-g200 or 4B7-gB9.7 by the substitution of the amino acid histidine (H, HIS) for at least one native amino acid as defined relative to the parental sequence. Specifically, a variant of 2A8-g200 may have any one of the following substitutions: VL-Y31H, VH-Y102H, VH-Y100H, VH-Y32H, VL-F48H, VL-S50H, VL-Y49H, VL-L27H, VL-V45H, VL-W90H and combinations thereof.

Anti-TFPI antibody 2A8-g200 and 4B7-gB9.7 variants can bind to TFPI with high affinity and high specificity in vivo (see WO 2011/109452). FIG. 1 shows amino acid sequence information for 2A8-g200 and 4B7-gB9.7, as well as other 2A8 and 4B7 variants described in WO 2011/109452. Table 1 shows the corresponding SEQ ID NOs for the variable heavy and variable light chains for the 2A8 and 4B7 variants shown in FIG. 1.

TABLE 1

Corresponding SEQUENCE ID NOs of variable heavy and variable light chains of the human anti-TFPI antibodies shown in Figure 1.

| CHAIN | MAb | SEQ ID NO: |
|---|---|---|
| VH | 2A8 | SEQ ID NO: 1 |
|  | 2A8-127 | SEQ ID NO: 5 |
|  | 2A8-143 | SEQ ID NO: 6 |
|  | 2A8-200 | SEQ ID NO: 7 |
|  | 2A8-216 | SEQ ID NO: 8 |
|  | 2A8-227 | SEQ ID NO: 9 |
|  | 2A8-g200 | SEQ ID NO: 10 |
|  | 2A8-g216 | SEQ ID NO: 11 |
|  | 4B7 | SEQ ID NO: 3 |
|  | 4B7-B18.5 | SEQ ID NO: 19 |
|  | 4B7-B2.0 | SEQ ID NO: 20 |
|  | 4B7-B27.1 | SEQ ID NO: 21 |
|  | 4B7-B32.5 | SEQ ID NO: 22 |
|  | 4B7-B41.2 | SEQ ID NO: 23 |
|  | 4B7-B9.7 | SEQ ID NO: 24 |
|  | 4B7-gB9.7 | SEQ ID NO: 25 |
|  | 4B7-gB9.7-IgG | SEQ ID NO: 26 |
| VL | 2A8 | SEQ ID NO: 2 |
|  | 2A8-127 | SEQ ID NO: 12 |
|  | 2A8-143 | SEQ ID NO: 13 |
|  | 2A8-200 | SEQ ID NO: 14 |
|  | 2A8-216 | SEQ ID NO: 15 |
|  | 2A8-227 | SEQ ID NO: 16 |
|  | 2A8-g200 | SEQ ID NO: 17 |
|  | 2A8-g216 | SEQ ID NO: 18 |
|  | 4B7 | SEQ ID NO: 4 |
|  | 4B7-B18.5 | SEQ ID NO: 27 |
|  | 4B7-B2.0 | SEQ ID NO: 28 |
|  | 4B7-B27.1 | SEQ ID NO: 29 |
|  | 4B7-B32.5 | SEQ ID NO: 30 |
|  | 4B7-B41.2 | SEQ ID NO: 31 |
|  | 4B7-B9.7 | SEQ ID NO: 32 |
|  | 4B7-gB9.7 | SEQ ID NO: 33 |
|  | 4B7-gB9.7-IgG | SEQ ID NO: 34 | pH sensitive variants of 2A8-g200 and 4B7-gB9.7 were created by subjecting both the CDR domains and the residues contacting the TFPI to analysis for binding characteristics upon mutagenesis at selected sites. FIG. 2 shows the location of possible His mutations for: A. 2A8-g200 (designated as A200 in FIG. 2A) variable heavy chain; B. 2A8-g200 (designated as A200 in FIG. 2B) variable light chain; C. 4B7-gB9.7 variable heavy chain; and D. 4B7-gB9.7 variable light chain. One histidine residue was substituted for each of the amino acids in either 1) a contact residue to TFPI as indicated by an underlined amino acid in FIG. 2, or 2) a CDR 1-3 residue as indicated by an asterisk in FIG. 2 for the anti-TFPI antibodies 2A8-g200 and 4B7-gB9.7. As shown in FIGS. 2A and 2B, forty (40) residues from the heavy chain and twenty-nine (29) residues from the light chain were identified as the positions for mutagenesis in 2A8-g200. As shown in FIGS. 2C and 2D, forty (40) heavy chain and thirty-two (32) light chain variants were identified in 4B7-gB9.7.

A 2A8-g200 Fab histidine scanning library was synthesized. The library contained 69 members. The 2A8-g200 Fab histidine library was cloned into a bacterial expression vector and the amino acid sequences were verified.

Sixty-nine (69) clones from the His scan library were transformed into *E. coli* ATCC strain 9637 and grown on selective media containing carbenecillin (100 μg/mL). Single colonies were used to inoculate LB-Carbenecillin-100 media. The cultures were grown to OD600=0.5 at 37° C., induced with 0.25 mM IPTG, and grown overnight at 30° C. The bacterial expression cultures were harvested by centrifugation at 5,000×g for 15 min at 4° C. The expression media was decanted from the pellet. Both pellet and cleared expression media were frozen at −20° C. The His muteins were purified from the expression media with Protein A. Purified muteins were analysed by SDS-PAGE and a concentration was obtained by A280.

Human TFPI, 1 μg/ml, was used to coat Maxisorb™ microtiter plates. Expression media, 100 μl, from each member of the His scan library, was added to two wells on the plate, in a pair wise fashion. The plate was incubated on a shaker at room temperature for 1 hr. The plate was washed 3× with PBST. PBS (pH 7.0) was added to one well of the pair, 100 mM pH6.0 Citrate buffer was added to the second well of the same pair. The plate was incubated at 37° C. with shaking for one hr. The plate was washed 3× with PBST and developed using amplex red. A pH 7.0/pH 6.0 ratio was established to rank the sensitive muteins. The ratio for wild type 2A8-g200 Fab was 1.0. The 10 clones that had a ratio greater than 1.78 between pH 7.0 and pH 6.0 are shown in Table 2 below.

TABLE 2 pH 6.0 TFPI Dissociation ELISA

| Rank | Mutation | TFPI ELISA pH 7.0 | pH 6.0 | Ratio pH 7.0/pH 6.0 |
|---|---|---|---|---|
| | wt gA200Fab | 5248 | 5354 | 0.98 |
| 1 | VL-Y31H | 913 | 133 | 6.64 |
| 2 | VH-Y102H | 3310 | 1079 | 3.07 |
| 3 | VH-Y100H | 2545 | 1431 | 1.78 |
| 4 | VH-Y32H | 3560 | 2585 | 1.38 |
| 5 | VL-F48H | 2068 | 1551 | 1.33 |
| 6 | VH-S50H | 2159 | 1637 | 1.32 |
| 7 | VL-Y49H | 2661 | 2044 | 1.3 |
| 8 | VL-L27H | 3422 | 2637 | 1.3 |
| 9 | VL-V45H | 2197 | 1771 | 1.24 |
| 10 | VL-W90H | 1833 | 1509 | 1.21 |

Purified 2A8-g200 variants in Fab format (referred to as wt gA200Fab in Table 1) were tested using surface plasmon resonance (Biacore). Surface plasmon resonance (Biacore T200) was used to measure the dissociation rate of the antibodies. Human TFPI (American Diagnostica) was amine coupled on a CM4 or CM5 chip using the method suggested by Biacore, resulting in 100 to 300 RU of immobilized TFPI. Purified 2A8-g200 variants were injected, following by 40-minute dissociation either at pH7.4 or pH6.0 buffer. The antibodies were diluted in HBS-P buffer at different concentrations and the flow rate was set to 50 μl/min. After each round of antibody injection, the chip was regenerated by injecting 90 μl of pH 1.5 glycine. The data set was evaluated using BIAevaluation Software.

The dissociation constant (kd) for each 2A8-g200 variant antibody was determined by using a model with the following equation:

$$R=R_0e^{-kd(t-t0)}+\text{offset}$$

where R is the response at time t, $R_0$ is the response at time $t_0$.—the start of dissociation, offset allows for a residual response at the end of complete dissociation. A ratio of kd at pH 6.0 to kd at pH 7.4 was calculated for each 2A8-g200 variant. A mutation with observed ratio of 2 was considered as pH-sensitive mutation and could be used for construction of IgG variants of 2A8-g200.

For example, referring to FIG. 3, observed variations in dissociation constant responses in the biocore assay at two different pHs (pH 6.0 and pH 7.4) are shown for two exemplary 2A8-g100 light chain histidine substitution mutations: A. L-L27H and B. L-Y31H.

Pharmacokinetic parameters of the antibodies were determined after intravenous (i.v.) bolus administration to HemA mouse at 2 mg/kg. All the pharmacokinetic parameters were calculated using WinNonLin software version 5.3.1 (Pharsight Corporation, Mountain View, Calif.) non-compartmental model. The effect of histidine mutations on the observed half-life of anti-TFPI monoclonal antibodies in mouse plasma is shown in FIG. 4. 2A8-g200 with the histidine mutations TPP2256 (L-Y31H/Y49H) and TPP2259 (L-Y31H) increased the observed pK profiles over a 500 hour time span as compared to the corresponding pK profile of 2A8-g200 without any histidine substitution. Table 3 quantifies the increases in half-life observed in the data of FIG. 4.

TABLE 3 pK parameters

| Antibody | Dose (mg/kg) | T ½ (hr) |
|---|---|---|
| 2A8-g200 | 2 | 71 |
| TTP-2256 | 2 | ~331 |
| TTP-2259 | 2 | ~437 |

Therefore, the above designated antibodies that reduce TFPI mediated TMDD and have a prolonged T½ would lead to less frequent dosing and reduce the amount of material needed per dose. Furthermore, the need for a lower dose may also make feasible subcutaneous dosing where the dosing volume becomes a limiting step, a process by which the antibody is removed from circulation due to its interaction with a rapidly cleared target or by being sequestered from the plasma due to its co-localization with its target.

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims. All references, patents, or other publications are specifically incorporated by reference herein.

The invention claimed is:

1. A variant of human monoclonal IgG antibody that binds specifically to human tissue factor pathway inhibitor (TFPI), which comprises a variable light chain domain and a variable heavy chain domain, and has increased plasma half-life as compared to the parental human monoclonal IgG antibody, wherein the variant antibody further comprises:
   a variable heavy chain domain defined by parental SEQ ID NO: 17, which comprises a histidine substitution selected from the group consisting of Y102H, Y32H and Y100H, and combinations thereof; and
   the variant antibody binds to TFPI at pH 7.0 with at least two fold higher affinity than at pH 6.0.

2. A variant of human monoclonal IgG antibody that binds specifically to human tissue factor pathway inhibitor (TFPI), which comprises a variable light chain domain and a variable heavy chain domain, and has increased plasma half-life as compared to the parental human monoclonal IgG antibody, wherein the variant antibody further comprises:
   a variable light chain domain defined by parental SEQ. ID. NO. 10, which comprises a histidine substitution selected from the group consisting of Y31H, F48H, Y49H, L27H, V45H, W90H and combinations thereof; and
   the variant antibody binds to TFPI at pH 7.0 with at least two fold higher affinity than at pH 6.0.

3. The variant antibody of claim 1, further comprising the variable light chain domain of SEQ ID NO: 10.

4. The variant antibody of claim 1, further comprising a variable light chain domain defined by parental SEQ. ID. NO. 10, which comprises a histidine substitution selected from the group consisting of Y31H, F48H, Y49H, L27H, V45H, W90H, and combinations thereof.

5. The variant of claim 2, further comprising the variable heavy chain domain of SEQ ID NO: 17.

6. A pharmaceutical composition comprising the variant antibody of claims 1, 2, 3, 4, or 5 and a pharmaceutically acceptable carrier.

\* \* \* \* \*

SEQUENCE LISTING

<160> NUMBER OF SEQ ID NOS: 34

<210> SEQ ID NO 1

```
<211> LENGTH: 117
<212> TYPE: PRT
<213> ORGANISM: Homo sapiens

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Ser Trp Val Arg Gln Ala Pro Gly Lys Gly Leu Glu Trp Val
        35                  40                  45

Ser Ser Ile Arg Gly Ser Ser Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Tyr Arg Tyr Trp Phe Asp Tyr Trp Gly Gln Gly Thr Leu
            100                 105                 110

Val Thr Val Ser Ser
        115

<210> SEQ ID NO 2
<211> LENGTH: 108
<212> TYPE: PRT
<213> ORGANISM: Homo sapiens

<400> SEQUENCE: 2

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Tyr
        35                  40                  45

Tyr Asp Asn Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Gly Val Pro Val
                85                  90                  95

Phe Gly Gly Gly Thr Lys Leu Thr Val Leu Gly Gln
            100                 105

<210> SEQ ID NO 3
<211> LENGTH: 123
<212> TYPE: PRT
<213> ORGANISM: Homo sapiens

<400> SEQUENCE: 3

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Asp Tyr Ala
50                  55                  60
```

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Tyr
            100                 105                 110

Trp Gly Gln Gly Thr Leu Val Thr Val Ser Ser
            115                 120

<210> SEQ ID NO 4
<211> LENGTH: 114
<212> TYPE: PRT
<213> ORGANISM: Homo sapiens

<400> SEQUENCE: 4

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Ser
            20                  25                  30

Asp Gly Asn Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr

<210> SEQ ID NO 5
<211> LENGTH: 117
<212> TYPE: PRT
<213> ORGANISM: Artificial
<220> FEATURE:
<223> OTHER INFORMATION: Variant

<400> SEQUENCE: 5

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gly Thr Leu
            100                 105                 110

Val Thr Val Ser Ser
            115

<210> SEQ ID NO 6

```
<211> LENGTH: 117
<212> TYPE: PRT
<213> ORGANISM: Artificial
<220> FEATURE:
<223> OTHER INFORMATION: Variant

<400> SEQUENCE: 6

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115

<210> SEQ ID NO 7
<211> LENGTH: 117
<212> TYPE: PRT
<213> ORGANISM: Artificial
<220> FEATURE:
<223> OTHER INFORMATION: Variant

<400> SEQUENCE: 7

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115

<210> SEQ ID NO 8
<211> LENGTH: 117
<212> TYPE: PRT
<213> ORGANISM: Artificial
<220> FEATURE:
<223> OTHER INFORMATION: Variant

<400> SEQUENCE: 8

Gln Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Arg Val Tyr
            20                  25                  30

Gly Met Ser Trp Val Arg Gln Ala Pro Gly Lys Gly Leu Glu Trp Val
        35                  40                  45

Ser Ser Asp Arg Gly Ser Arg Ser Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Arg Tyr Trp Phe Asp Tyr Trp Gly Gln Gly Thr Leu
            100                 105                 110

Val Thr Val Ser Ser
        115

<210> SEQ ID NO 9
<211> LENGTH: 117
<212> TYPE: PRT
<213> ORGANISM: Artificial
<220> FEATURE:
<223> OTHER INFORMATION: Variant

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Ser Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115

<210> SEQ ID NO 10
<211> LENGTH: 117
<212> TYPE: PRT
<213> ORGANISM: Artificial
<220> FEATURE:
<223> OTHER INFORMATION: Variant

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Arg Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115

<210> SEQ ID NO 11
<211> LENGTH: 117
<212> TYPE: PRT
<213> ORGANISM: Artificial
<220> FEATURE:
<223> OTHER INFORMATION: Variant

<400> SEQUENCE: 11

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Val Tyr
            20                  25                  30

Gly Met Ser Trp Val Arg Gln Ala Pro Gly Lys Gly Leu Glu Trp Val
        35                  40                  45

Ser Ser Asp Arg Gly Ser Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Arg Tyr Trp Phe Asp Tyr Trp Gly Gln Gly Thr Leu
            100                 105                 110

Val Thr Val Ser Ser
        115

<210> SEQ ID NO 12
<211> LENGTH: 108
<212> TYPE: PRT
<213> ORGANISM: Artificial
<220> FEATURE:
<223> OTHER INFORMATION: Variant

<400> SEQUENCE: 12

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Phe
        35                  40                  45

Tyr Asp Val Asn Arg Pro Ser Asp Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Asp Gly Val Pro Trp
                85                  90                  95

Phe Gly Gly Gly Thr Lys Leu Thr Val Leu Gly Gln
            100                 105

<210> SEQ ID NO 13
<211> LENGTH: 108
<212> TYPE: PRT
```

```
<213> ORGANISM: Artificial
<220> FEATURE:
<223> OTHER INFORMATION: Variant

<400> SEQUENCE: 13

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Ile Phe
        35                  40                  45

Tyr Asp Val Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Leu Asp Gly Val Pro Trp
                85                  90                  95

Phe Gly Gly Gly Thr Lys Leu Thr Val Leu Gly Gln
            100                 105

<210> SEQ ID NO 14
<211> LENGTH: 108
<212> TYPE: PRT
<213> ORGANISM: Artificial
<220> FEATURE:
<223> OTHER INFORMATION: Variant

<400> SEQUENCE: 14

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Ile Phe
        35                  40                  45

Tyr Asp Val Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Trp Asp Gly Val Pro Val
                85                  90                  95

Phe Gly Gly Gly Thr Lys Leu Thr Val Leu Gly Gln
            100                 105

<210> SEQ ID NO 15
<211> LENGTH: 108
<212> TYPE: PRT
<213> ORGANISM: Artificial
<220> FEATURE:
<223> OTHER INFORMATION: Variant

<400> SEQUENCE: 15

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Ile Phe
        35                  40                  45

Tyr Asp Asn Asn Arg Pro Ser Gly Ile Pro Glu Arg Phe Ser Gly Ser
    50                  55                  60
```

```
Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Trp Leu Asp Gly Val Pro Trp
                 85                  90                  95

Phe Gly Gly Gly Thr Lys Leu Thr Val Leu Gly Gln
            100                 105

<210> SEQ ID NO 16
<211> LENGTH: 108
<212> TYPE: PRT
<213> ORGANISM: Artificial
<220> FEATURE:
<223> OTHER INFORMATION: Variant

<400> SEQUENCE: 16

Asp Ile Glu Leu Thr Gln Pro Pro Ser Val Ser Val Ala Pro Gly Gln
  1               5                  10                  15

Thr Ala Arg Ile Ser Cys Ser Gly Asp Asn Leu Arg Asn Tyr Tyr Ala
                 20                  25                  30

His Trp Tyr Gln Gln Lys Pro Gly Gln Ala Pro Val Val Val Ile Phe
             35                  40                  45

Tyr Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Trp Leu Asp Gly Val Pro Trp
                 85                  90                  95

Phe Gly Gly Gly Thr Lys Leu Thr Val Leu Gly Gln
            100                 105

<210> SEQ ID NO 17
<211> LENGTH: 108
<212> TYPE: PRT
<213> ORGANISM: Artificial
<220> FEATURE:
<223> OTHER INFORMATION: Variant

<400> SEQUENCE: 17

Ser Tyr Glu Leu Thr Gln Pro Pro Ser Val Ser Val Ser Pro Gly Gln
  1               5                  10                  15

Thr Ala Arg Ile Thr Cys Ser Gly Asp Asn Leu Pro Lys Tyr Tyr Ala
                 20                  25                  30

His Trp Tyr Gln Gln Lys Pro Gly Gln Ala Pro Val Val Val Ile Phe
             35                  40                  45

Tyr Asp Val Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Trp Ser Ser Thr Pro Val
                 85                  90                  95

Phe Gly Gly Gly Thr Lys Leu Thr Val Leu Gly Gln
            100                 105

<210> SEQ ID NO 18
<211> LENGTH: 108
<212> TYPE: PRT
<213> ORGANISM: Artificial
<220> FEATURE:
<223> OTHER INFORMATION: Variant
```

<400> SEQUENCE: 18

Ser Tyr Glu Leu Thr Gln Pro Pro Ser Val Ser Val Ser Pro Gly Gln
1               5                   10                  15

Thr Ala Arg Ile Thr Cys Ser Gly Asp Asn Leu Pro Lys Tyr Tyr Ala
            20                  25                  30

His Trp Tyr Gln Gln Lys Pro Gly Gln Ala Pro Val Val Val Ile Phe
        35                  40                  45

Tyr Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ser Trp Leu Ser Gly Thr Pro Trp
                85                  90                  95

Phe Gly Gly Gly Thr Lys Leu Thr Val Leu Gly Gln
            100                 105

<210> SEQ ID NO 19
<211> LENGTH: 123
<212> TYPE: PRT
<213> ORGANISM: Artificial
<220> FEATURE:
<223> OTHER INFORMATION: Variant

<400> SEQUENCE: 19

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Gln Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120

<210> SEQ ID NO 20
<211> LENGTH: 123
<212> TYPE: PRT
<213> ORGANISM: Artificial
<220> FEATURE:
<223> OTHER INFORMATION: Variant

<400> SEQUENCE: 20

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Arg Tyr Ala
    50                  55                  60

```
Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120

<210> SEQ ID NO 21
<211> LENGTH: 123
<212> TYPE: PRT
<213> ORGANISM: Artificial
<220> FEATURE:
<223> OTHER INFORMATION: Variant

<400> SEQUENCE: 21

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asp
             20                  25                  30

Ser Ala Ala Trp Ser Trp Ile Arg Gln Ser Pro Gly Arg Gly Leu Glu
         35                  40                  45

Trp Leu Gly Ile Ile Tyr Lys Arg Ser Lys Trp Tyr Asn Arg Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120

<210> SEQ ID NO 22
<211> LENGTH: 123
<212> TYPE: PRT
<213> ORGANISM: Artificial
<220> FEATURE:
<223> OTHER INFORMATION: Variant

<400> SEQUENCE: 22

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Ser Trp Ile Arg Gln Ser Pro Gly Arg Gly Leu Glu
         35                  40                  45

Trp Leu Gly Ile Ile Tyr Lys Arg Ser Lys Trp Tyr Asn Arg Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
```

<210> SEQ ID NO 23
<211> LENGTH: 123
<212> TYPE: PRT
<213> ORGANISM: Artificial
<220> FEATURE:
<223> OTHER INFORMATION: Variant

<400> SEQUENCE: 23

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120

<210> SEQ ID NO 24
<211> LENGTH: 123
<212> TYPE: PRT
<213> ORGANISM: Artificial
<220> FEATURE:
<223> OTHER INFORMATION: Variant

<400> SEQUENCE: 24

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120

<210> SEQ ID NO 25
<211> LENGTH: 123
<212> TYPE: PRT
<213> ORGANISM: Artificial
<220> FEATURE:
<223> OTHER INFORMATION: Variant

<400> SEQUENCE: 25

```
Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Ser Arg Gly Leu Glu
        35                  40                  45

Trp Leu Gly Ile Ile Tyr Tyr Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
            115                 120
```

<210> SEQ ID NO 26
<211> LENGTH: 123
<212> TYPE: PRT
<213> ORGANISM: Artificial
<220> FEATURE:
<223> OTHER INFORMATION: Variant

<400> SEQUENCE: 26

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Ser Arg Gly Leu Glu
        35                  40                  45

Trp Leu Gly Ile Ile Tyr Tyr Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
            115                 120
```

<210> SEQ ID NO 27
<211> LENGTH: 114
<212> TYPE: PRT
<213> ORGANISM: Artificial
<220> FEATURE:
<223> OTHER INFORMATION: Variant

<400> SEQUENCE: 27

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ile Ser
            20                  25                  30

Phe Gly Ile Thr Tyr Leu Asn Trp Tyr Leu Gln Lys Pro Gly Gln Ser
            35                  40                  45

Pro Gln Leu Leu Ile Tyr Lys Gly Ser Asn Arg Ala Ser Gly Val Pro
```

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Asp Ser Tyr Pro Leu Thr Phe Gly Gln Gly Thr Lys Val Glu Ile Lys
                100                 105                 110

Arg Thr

<210> SEQ ID NO 28
<211> LENGTH: 114
<212> TYPE: PRT
<213> ORGANISM: Artificial
<220> FEATURE:
<223> OTHER INFORMATION: Variant

<400> SEQUENCE: 28

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Phe Arg
                 20                  25                  30

Phe Gly Ile Thr Tyr Leu Asn Trp Tyr Leu Gln Lys Pro Gly Gln Ser
                 35                  40                  45

Pro Gln Leu Leu Ile Tyr Lys Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Thr Ser Tyr Pro Leu Thr Phe Gly Gln Gly Thr Lys Val Glu Ile Lys
                100                 105                 110

Arg Thr

<210> SEQ ID NO 29
<211> LENGTH: 114
<212> TYPE: PRT
<213> ORGANISM: Artificial
<220> FEATURE:
<223> OTHER INFORMATION: Variant

<400> SEQUENCE: 29

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Phe Ser
                 20                  25                  30

Asp Gly Thr Thr Tyr Leu Asn Trp Tyr Leu Gln Lys Pro Gly Gln Ser
                 35                  40                  45

Pro Gln Leu Leu Ile Tyr Lys Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Thr Ser Tyr Pro Leu Thr Phe Gly Gln Gly Thr Lys Val Glu Ile Lys
                100                 105                 110

Arg Thr
```

```
<210> SEQ ID NO 30
<211> LENGTH: 114
<212> TYPE: PRT
<213> ORGANISM: Artificial
<220> FEATURE:
<223> OTHER INFORMATION: Variant

<400> SEQUENCE: 30

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Ser
            20                  25                  30

Phe Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr

<210> SEQ ID NO 31
<211> LENGTH: 114
<212> TYPE: PRT
<213> ORGANISM: Artificial
<220> FEATURE:
<223> OTHER INFORMATION: Variant

<400> SEQUENCE: 31

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Arg
            20                  25                  30

Phe Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr

<210> SEQ ID NO 32
<211> LENGTH: 114
<212> TYPE: PRT
<213> ORGANISM: Artificial
<220> FEATURE:
<223> OTHER INFORMATION: Variant

<400> SEQUENCE: 32

Asp Ile Val Met Thr Gln Ser Pro Leu Ser Leu Pro Val Thr Pro Gly
1               5                   10                  15
```

Glu Pro Ala Ser Ile Ser Cys Arg Ser Ser Gln Ser Leu Val Phe Arg
            20                  25                  30

Asp Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr

<210> SEQ ID NO 33
<211> LENGTH: 114
<212> TYPE: PRT
<213> ORGANISM: Artificial
<220> FEATURE:
<223> OTHER INFORMATION: Variant

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Arg
            20                  25                  30

Asp Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr

<210> SEQ ID NO 34
<211> LENGTH: 114
<212> TYPE: PRT
<213> ORGANISM: Artificial
<220> FEATURE:
<223> OTHER INFORMATION: Variant

<400> SEQUENCE: 34

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Arg
            20                  25                  30

Asp Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr

-continued

```
                85                  90                  95
Asp Ser Tyr Pro Leu Thr Phe Gly Gln Gly Thr Lys Val Glu Ile Lys
            100                 105                 110
Arg Thr
```